United States Patent [19]

Wathelet

[11] Patent Number: 4,650,172
[45] Date of Patent: Mar. 17, 1987

[54] TILTING EXAMINATION FRAME

[75] Inventor: Daniel Wathelet, Richelle-Vise, Belgium

[73] Assignee: Thomson-CGR, Paris, France

[21] Appl. No.: 589,321

[22] Filed: Mar. 14, 1984

[30] Foreign Application Priority Data

Mar. 18, 1983 [FR] France .................................. 83 04483

[51] Int. Cl.⁴ ............................................. G03B 41/16
[52] U.S. Cl. ..................................... 269/323; 378/209
[58] Field of Search ................ 269/325; 378/208, 209; 108/1, 7

[56] References Cited

U.S. PATENT DOCUMENTS 4,019,059 4/1977 Brundin et al. ...................... 378/209
4,481,657 11/1984 Larsson ................................ 378/204

FOREIGN PATENT DOCUMENTS 2026206 7/1979 United Kingdom .

Primary Examiner—Robert C. Watson

[57] ABSTRACT

The invention concerns a simplified control tilting examination frame. According to the invention, the frame comprises a table, a base and a pivoting support while the control system of the displacement of the table with respect to the support is servo-controlled by a representative signal of the tilting of the said pivoting support, in order to prevent under any circumstances one end of the table from touching the ground. The invention applies to medical radiology.

3 Claims, 5 Drawing Figures

FIG_1
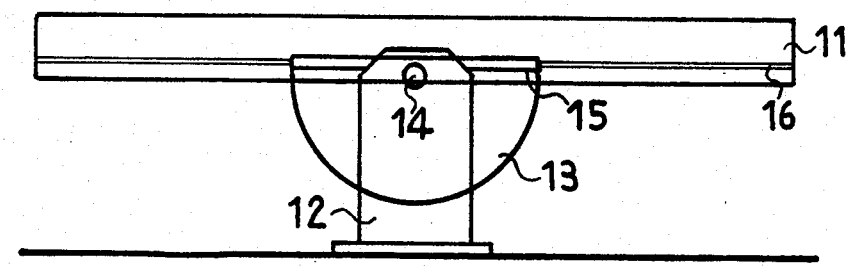
FIG_2
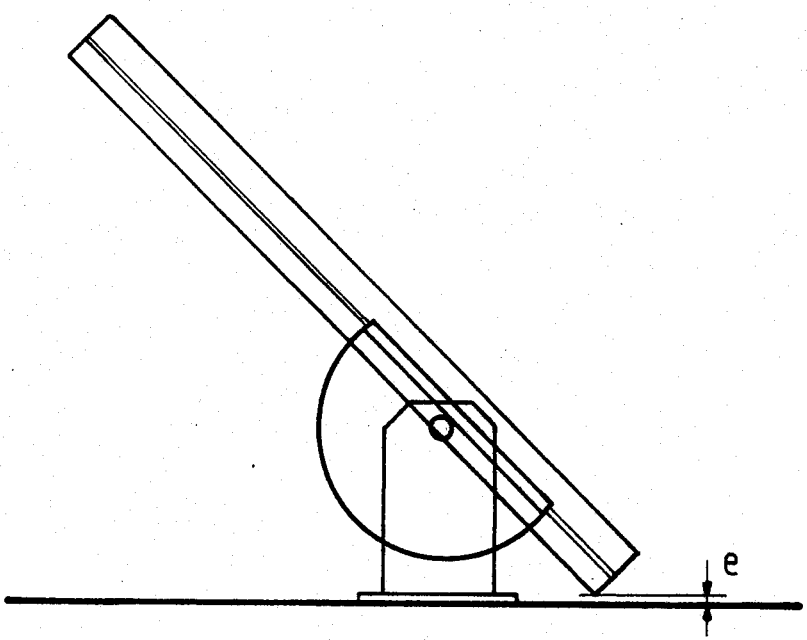
FIG_3
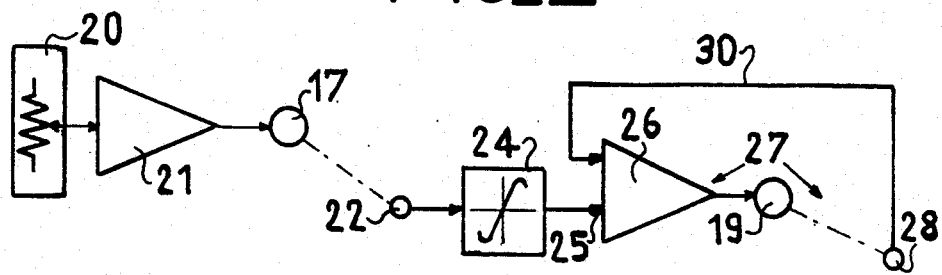

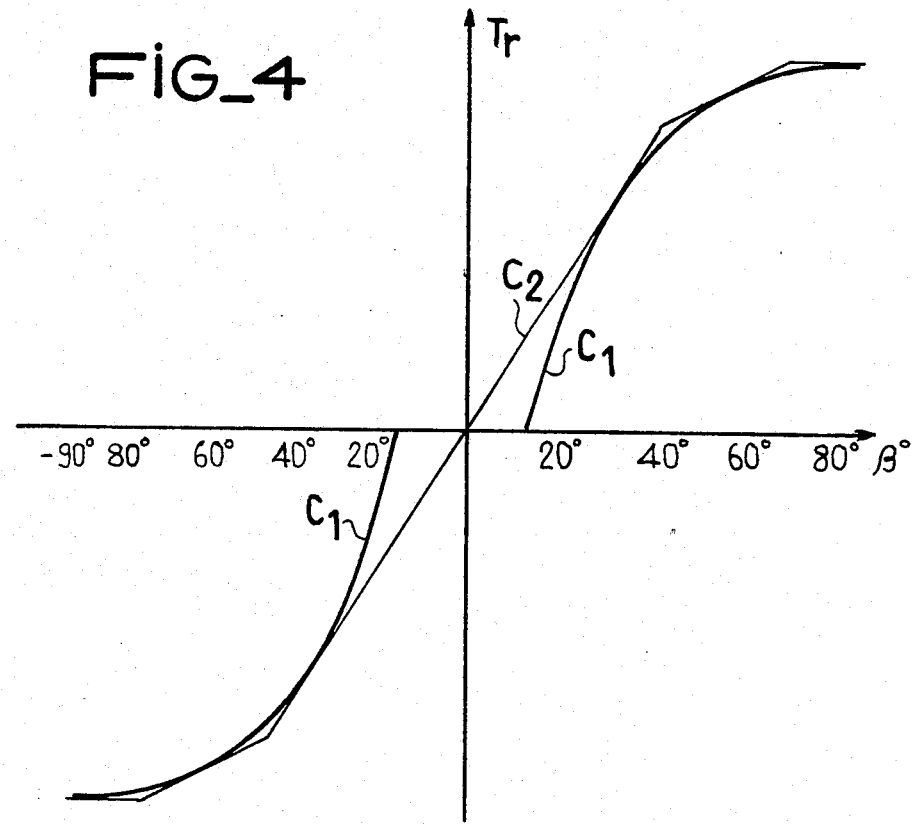
FIG_4
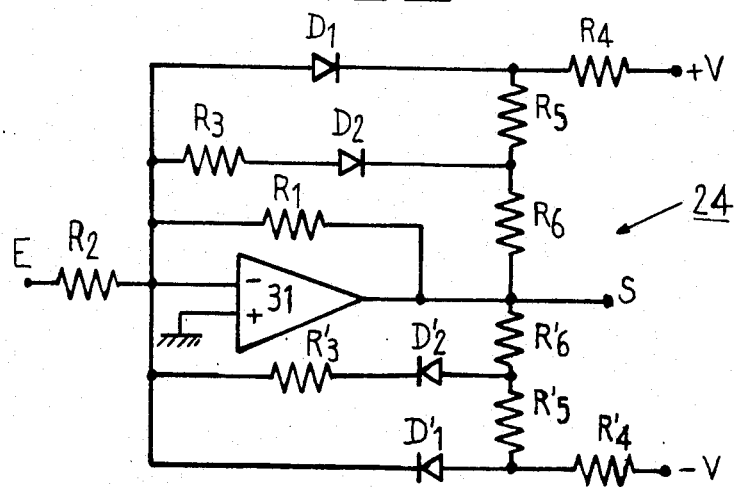
FIG_5

TILTING EXAMINATION FRAME

The invention concerns a tilting examination frame, especially for radiology installations. More particularly, its object is to combine table tilting and translation movements, with the aim of simplifying control and avoiding incorrect operating movement.

BACKGROUND OF THE INVENTION

In radiology, it is often necessary to pivot the examination frame on which the patient is positioned, up to extreme positions close to ±90° C. with respect to the horizontal position of the examination table. This table is fairly long so that simply tilting it with respect to its pedestal or base is not sufficient to ensure it has an appropriate pivoting possibility. One end of the table would touch the ground fairly rapidly under these conditions.

FIELD OF THE INVENTION

The Invention allows to overcome this problem to the extent that It proposes on the one hand oonferring on the table a double movement, namely a rotation and translation movement with respect to the base in order to increase the maximum pivoting angle and on the other hand rendering these movements contingent upon eaoh other in order to ellminate any risk of incorrect manoeuvre by the operator, who only disposes of a single control, i.e. that of pivoting.

In this aim, the invention concerns therefore a tilting examination frame, especially for radiology installations, comprising a table, moveable with respect to the fixed base, wherein said frame comprises:

- a tilting support, mounted in rotation with respect to the said base about a horizontal axis and on which the said table is mounted moveable parallel-wise to its longitudinal direction,
- first controlled motor means, disposed to bring about the rotation of the said tilting support with respect to the said base, and
- second controlled motor means disposed to displace linear-wise the said table with respect to the said tilting support, and wherein a control signal generator means of the second motor means is monitored by the movement of the said first motor means.

BRIEF DESCRIPTION OF THE DRAWINGS

The invention will be more clearly understood and further its advantages will appear from reading through the following description of an examination frame according to the invention, given by way of nonlimitative example, with reference to the annexed drawings in which:

FIG. 1 is a schematic view of an examination frame, with the table in horizontal position;

FIG. 2 represents the same frame with the table in an extreme tilted position;

FIG. 3 is a general block diagram of the control system of the motor means of the two movements of the frame;

FIG. 4 represents a first graph illustrating the law of variation necessary between the angle of rotation and the amplitude of translation of the table in order to obtain a controlled ground clearance as well as a second graph constituting a possible approximation of this law; and FIG. 5 is a non-linear circuit diagram.

DESCRIPTION OF THE PREFERRED EMBODIMENT

FIGS. 1 and 2 show that the tilting examination frame according to the invention comprises essentially a table 11, a fixed base 12 and a tilting support 13. This support is mounted in rotation with respect to the base 12 about a horizontal axis 14. It comprises, furthermore, two parallel slide-elements 15 located respectively on either side of the table 11. They are engaged in corresponding slide-elements 16 fixed along the longitudinal edges of the said table. The tilting of the support 13 with respect to the base 12 is ensured by an electric motor 17 (FIG. 3) through the intermediary of a reducer (not represented). The lay-out of this reducer is conventional and does not form part of the invention; according to one preferred embodiment it comprises a belt stage followed by a screw reducer and a stage with sprocket and chain wound on a sector integral with the tilting axis 14. The displacement of the table 11 in the slide-element 15 of the tilting support is also ensured by an electric-motor 19 (FIG. 3) through the intermediary of another reducer.

FIG. 2 illustrates the double movement that must be carried out by the table so as to be able to re-erect it almost completely without touching the ground. The tilting movement of the support 13 must be accompanied by an automatic translation of the table 11 with respect to this same support, so as to always maintain a minimum ground clearance e. This double movement is ensured by the control system schematized on FIG. 3.

The motor 17 described herein-above is guided by a known speed control circuit 21, of which a reference display element 20 (potentiometer or any other analog means) constitutes the sole adjustment means available to the operator. Rotation measurement means 22 (which can be a simple potentiometer) are mechanically associated with axis 14 or a chosen point of the tilting reducer described herein-above. It generates on exploitable electric signal representative of the tilting of the support 13 and this signal is applied, via a non-linear circuit 24, to the reference input 25 of a position servo-system 27 of the table 11 with respect to the tilting support 13. The servo-system, of course, controls the motor 19 and comprises a control circuit 26 of the said motor, which control circuit comprises a differential input, and measuring means 28 of the position of the table with respect to the said tilting support 13 (which measuring means can be a potentiometer) mechanically associated with the motor 19 and generating an exploitable electric signal reinjected as a counter-current (liaison 30) at the differential input of the control circuit 26. The maximum tilting speed is chosen slow enough for the servo-system to be able to "follow" without delay and so that at no moment does the end of the table risk dropping below the predetermined ground clearance e.

FIG. 4 illustrates how the transfer function of the non-linear circuit 24 is determined. The broken curve $C_1$, represents the required variation law of the translation amplitude Tr of the table 11 with respect to the tilting support in function of rotation angle beta of said support. It is determined graphically or trigonometrically in function of the dimensions of the base and of the table (height of the axis 14 with respect to the ground, length of the table, etc) and the predetermined ground clearance e. Thereafter, an approximate curve $C_2$ is defined by imposing a continuity at the origin in order to ensure a certain progressivity of the movement close to the horizontal position. Curve $C_2$ represents the transfer function of the non-linear circuit 24. This curve is constituted by linear sections of different lengths obtained by creating gain variations in the circuit 24 which variations are determined, for example, by diode means.

FIG. 5 is a possible scheme of such a non-linear circuit. This circuit comprises a diffential operational amplifier 31 the gain of which is essentially determined by the ratio between the resistance of counter-reaction $R_1$ and the input resistance $R_2$. A line or chain of resistances in series $R_4$, $R_5$, $R_6$ is connected between a source of positive voltage $+V$ and the output S of the non-linear circuit 24. Similarly, a chain of resistances in series $R_4'$, $R_5'$, $R_6'$, is connected between a negative voltage source $-V$ and the output S. A diode $D_1$ is connected between the common point of the resistance $R_1$ and $R_2$ and the common point of the resistances $R_4$ and $R_5$. A diode $D_1'$ is connected, in the opposite direction with respect to the diode $D_1$, between the common point of resistance $R_1$, $R_2$ and the common point of resistance $R_4'$ and $R_5'$. A connection in series of a diode $D_2$ and a resistance $R_3$ is made between the common point of resistances $R_1$ and $R_2$ and the common point of resistances $R_5$, $R_6$. A connection in series of a resistance $R_3'$ and a diode $D_2'$ is made between the common point of resistances $R_1$ and $R_2$ and the common point of resistances $R_5'$ and $R_6'$, the diode $D_2'$ being connected in the opposite direction of diode $D_2$. With this layout, the $D_1$ and $D_2$ diodes (or diodes $D_2'$ and $D_2'$ for negative angles) are conductive; this provokes changes of slope of curve $C_2$. The lengths of the constant slope sections of the curve $C_2$ are determined by voltage-dividers $R_4$, $R_5$, $R_6$, and $R_4'$, $R_5'$, $R_6'$.

Of course, the present invention is in no way limited to the embodiment described herein-above. In particular, the installation can indeed be realized in digital technology by possibly using step by step motors. The non-linear circuit would thus be, for example, a dead-memory constituting a conversion table. In other words, the present invention covers all the equivalent technical means brought into play, if these are within the framework of the following claims.

I claim:
1. An examination frame, especially for use in radiology, comprising:
   a fixed base supportable on a substantially horizontal surface;
   a support mounted to said base so as to be rotatable about a horizontal axis which is stationary with respect to the horizontal surface;
   an elongated table having a length more than twice the distance between said axis and said surface;
   means for slidably guiding said table on said support in longitudinal direciton of said table;
   fixed motor means for rotating said support about said horizontal axis;
   a first measuring means responsive to the output of said fixed motor means for generating a firsty signal proportional to the rotation angle of said table;
   second motor means for sliding said table relative to said support in longitudinal direction of said table;
   and motor control means connected to said first and second motor means, said motor control means including a second measuring means responsive to the output of said second motor means for generating a second signal proportional to the longitudinal position of said table with respect to said support a non-linear circuit means connected to said first measuring means to receive said first signal and having a transfer function means which changes said first signal into a third signal which is proportional to the longitudinal position of said table required to maintain a predetemined clearance between said table and the horizontal surface, said transfer function means including means for imposing a continuity of said third signal when said table rotation angle is approximately zero degrees, and control circuit means connected to said second measuring means to receive said second signal and to said non-linear circuit means to receive said third signal and having means for combining said second and third signals and generating a control signal for said second motor means;
   for controlling said second motor means such that a longitudinal end of said table maintains the predetermined clearance with respect to the horizontal surface.
2. An examination frame according to claim 1, wherein said measuring means is a potentiometer connected to said first motor means.
3. An emamination frame according to claim 1, wherein said non-linear circuit comprises an opertional amplifier having a plurality of resistive counter-reaction leads in parallel, and diodes in at least some of said leads.

* * * * *